United States Patent [19]

Dolak et al.

[11] 4,397,950

[45] Aug. 9, 1983

[54] **PROCESS FOR PRODUCTION OF ANTIBIOTIC U-64,767 USING *STREPTOMYCES MACRONENSIS* NRRL 12566**

[75] Inventors: Lester A. Dolak, Cooper Township, Kalamazoo County; Fritz Reusser, Portage; Thomas M. Castle, Cooper Township, Kalamazoo County; Betty R. Hannon; Alice L. Laborde, both of Kalamazoo Township, Kalamazoo County; Charles K. Marschke, Portage, all of Mich.

[73] Assignee: The Upjohn Company, Kalamazoo, Mich.

[21] Appl. No.: 324,246

[22] Filed: Nov. 23, 1981

[51] Int. Cl.³ .................. C12P 17/06; C12N 1/20; C12R 1/465
[52] U.S. Cl. .................. 435/125; 435/253; 435/886
[58] Field of Search .............. 435/68, 886, 899, 253, 435/125, 169; 424/116, 124

[56] References Cited

U.S. PATENT DOCUMENTS 3,515,717  6/1970  Cha et al. ................ 435/73

OTHER PUBLICATIONS

Bognar et al., *Acta. Chim. Acad. Sci. Hung.*, 56, 53–60, 1968.

*Primary Examiner*—Thomas G. Wiseman
*Assistant Examiner*—Kathleen S. McCowin
*Attorney, Agent, or Firm*—Roman Saliwanchik

[57] ABSTRACT

Novel antibiotic U-64,767 producible in a fermentation under controlled conditions using a biologically pure culture of the microorganism *Streptomyces macronensis* Dietz sp.n., NRRL 12566. This antibiotic is active against various Gram-positive bacteria, for example, *Staphylococcus aureus* and *Streptococcus pyogenes*. It is also active against the Gram-negative bacterium *Streptococcus pneumoniae*. Thus, antibiotic U-64,767 can be used in various environments to eradicate or control such bacteria.

4 Claims, 3 Drawing Figures

PROCESS FOR PRODUCTION OF ANTIBIOTIC U-64,767 USING *STREPTOMYCES MACRONENSIS* NRRL 12566

BRIEF SUMMARY OF THE INVENTION

Antibiotic U-64,767 is producible in a fermentation under controlled conditions using a biologically pure culture of the new microorganism *Streptomyces macronensis*, Dietz sp.n., NRRL 12566.

Antibiotic U-64,767 is active against various Gram-positive bacteria. Thus, antibiotic U-64,767 can be used to disinfect washed and stacked food utensils contaminated with *S. aureus*. It can also be used as a disinfectant on various dental and medical equipment contaminated with *S. aureus*. Still further, antibiotic U-64,767 can be used as a bacteriostatic rinse for laundered clothes, and for impregnating papers and fabrics; and it is also useful for suppressing the growth of sensitive organisms in plate assays and other microbiological media.

DETAILED DESCRIPTION OF THE INVENTION

Chemical and Physical Properties of Antibiotic U-64,767

Figure 2:
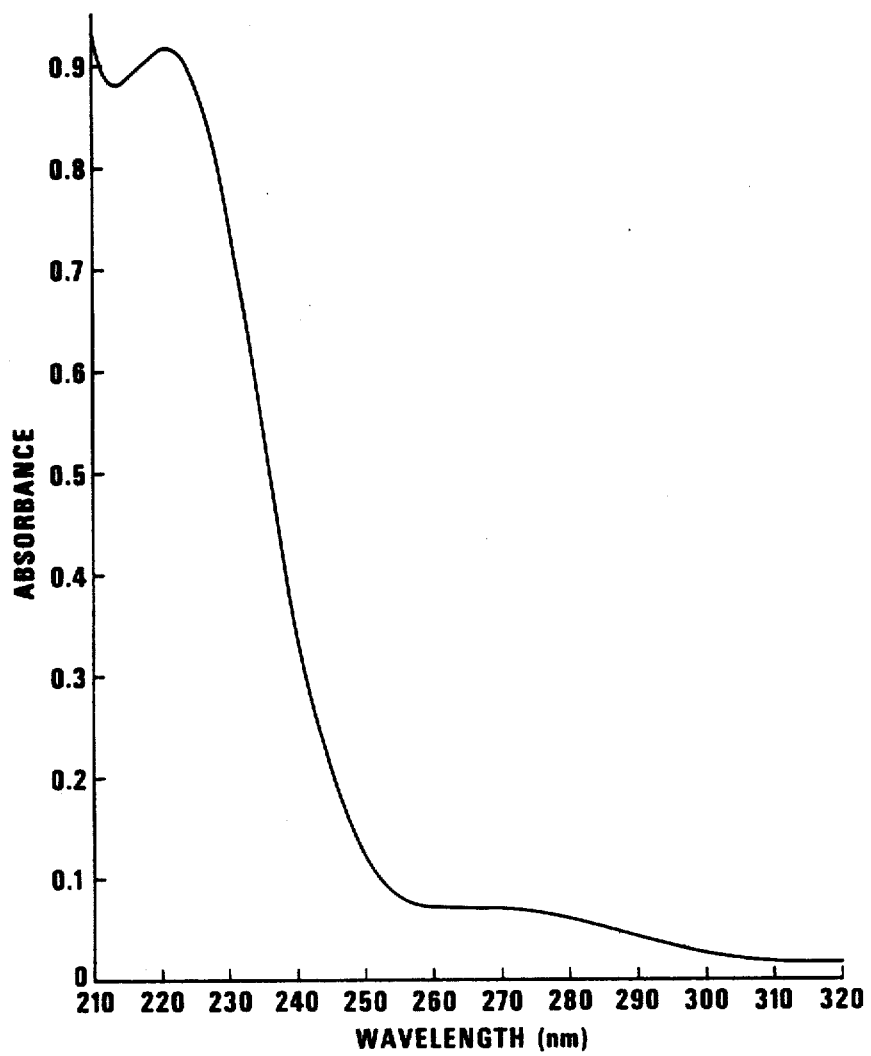

Molecular Weight: 1191 (mass spectrometry)
Molecular Formula: $C_{57}H_{109}N_1O_{24}$
Color of Pure Solid: White
Ultraviolet Absorption Spectrum:

The UV spectrum of antibiotic U-64,767 is shown in FIG. 2 of the drawings. At 0.1 mg/ml in 2:1 methanol:-water the absorbance at 223 nm is 1.25 as a distinct peak on end absorption.

Elemental Composition: C, 59.51; H, 9.17; N, 1.14; O, 32.65.

Figure 1:
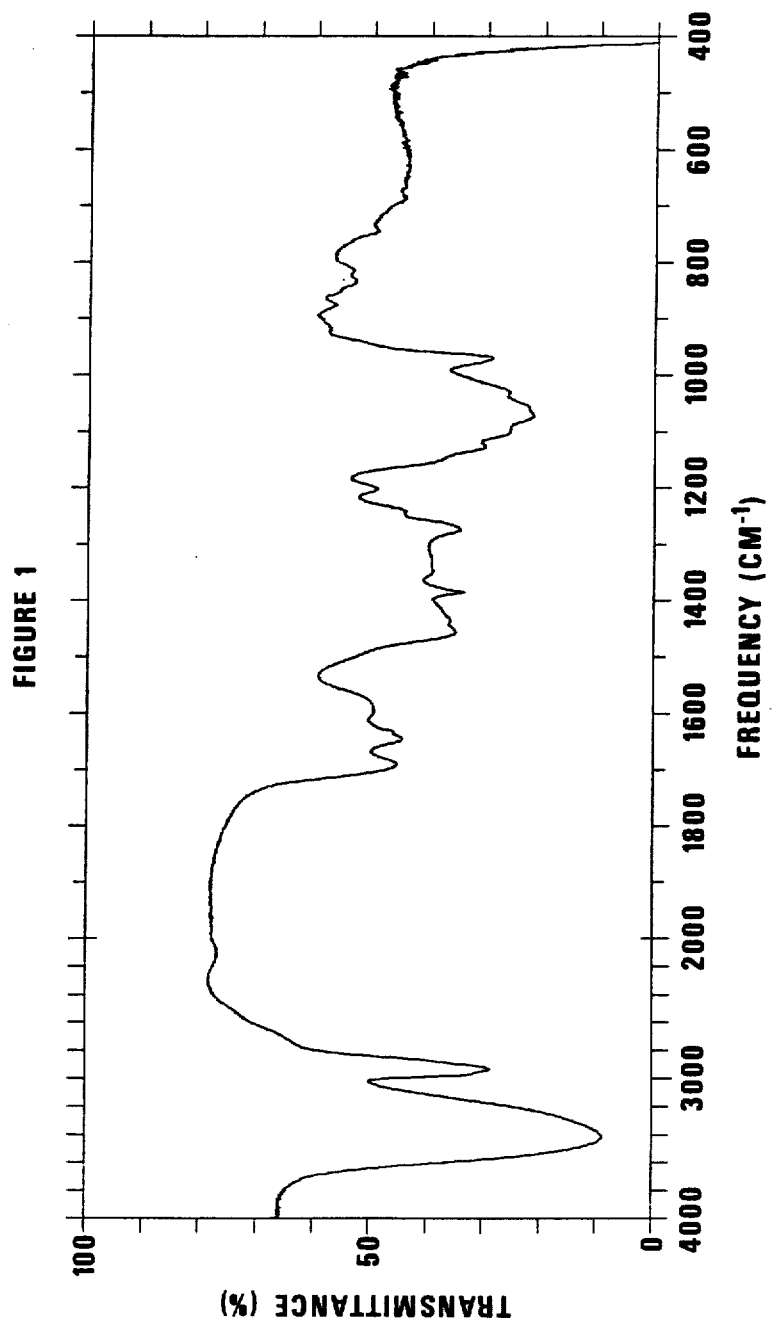

Melting Point: 153°–155° C. with decomposition.
Infrared Absorption Spectrum:

Antibiotic U-64,767 has a characteristic infrared absorption spectrum in a mineral oil mull as shown in FIG. 1 of the drawings. Peaks are observed at the following wave lengths.

| Band Freq.[1] | Inten.[2] | Type[3] | Band Freq. | Inten. | Type |
|---|---|---|---|---|---|
| 3375.8 | 7 | BRD | 1149.7 | 27 | AVG |
| 2953.3 | 0 | BRD M | 1126.5 | 21 | AVG |
| 2925.3 | 0 | BRD M | 1101.4 | 17 | AVG |
| 2854.9 | 2 | AVG M | 1071.5 | 14 | AVG |
| 2729.6 | 52 | BRD M | 1056.1 | 13 | AVG |
| 2691.0 | 55 | SH | 1030.1 | 17 | AVG |
| 1691.7 | 42 | AVG | 968.3 | 17 | AVG |
| 1646.4 | 44 | AVG | 917.2 | 51 | AVG |
| 1576.0 | 45 | BRD | 874.8 | 52 | AVG |
| 1456.4 | 8 | AVG M | 850.7 | 48 | SH |
| 1377.3 | 13 | AVG M | 833.3 | 44 | AVG |
| 1367.6 | 21 | SH M | 817.9 | 48 | SH |
| 1349.3 | 25 | AVG | 721.4 | 36 | AVG M |
| 1273.1 | 24 | AVG | 685.7 | 36 | AVG |
| 1241.3 | 34 | AVG | | | |
| 1201.7 | 42 | AVG | | | |

[1]Wavenumbers (cm$^{-1}$)
[2]Percent transmittance (% T);
[3]SH = shoulder
AVG = average
BRD = broad
Intensity at 3800 cm$^{-1}$ is 85% T.

Figure 3:
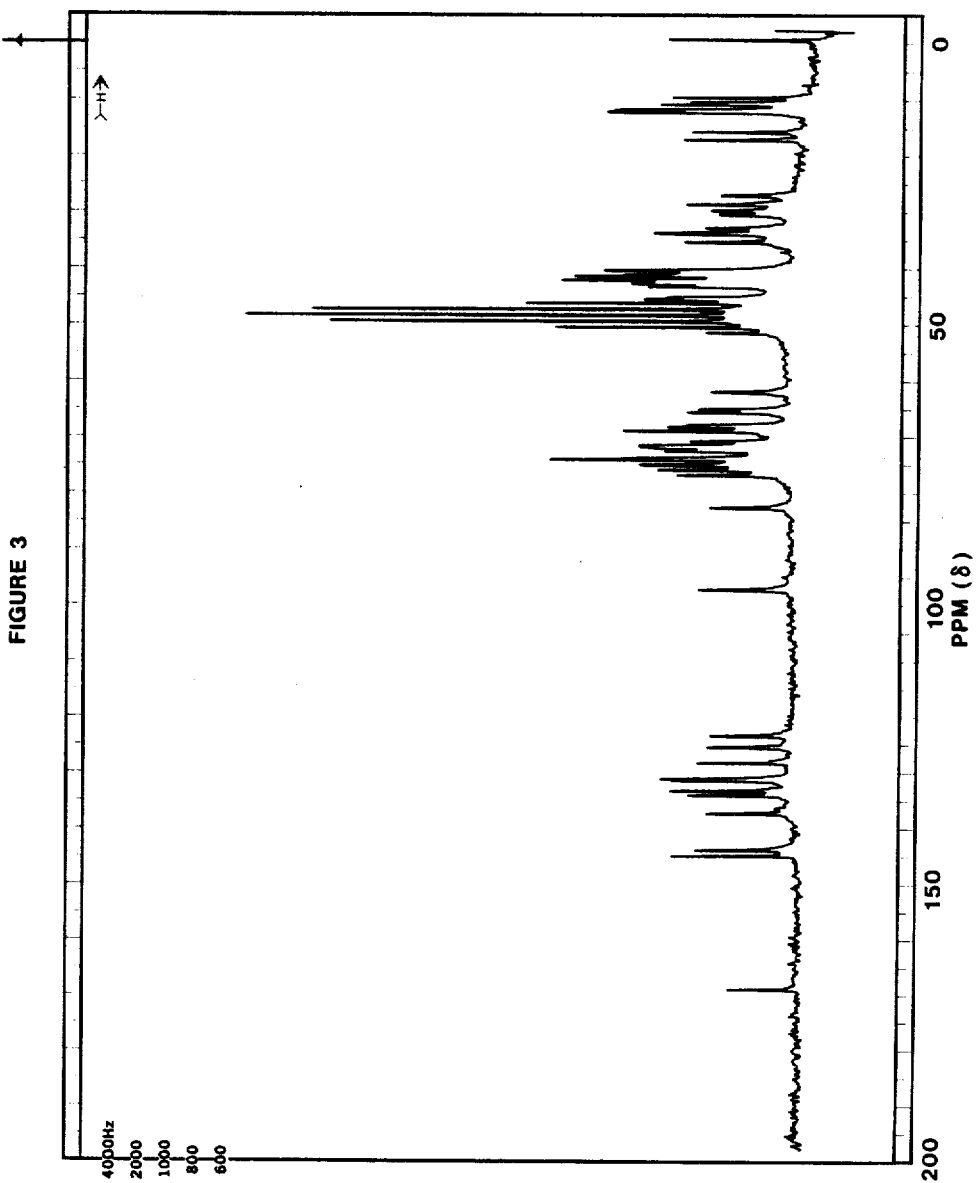

$^{13}$C-Nuclear Magnetic Resonance (NMR) Spectrum:
The $^{13}$C-NMR spectrum of antibiotic U-64,767 is shown in FIG. 3 of the drawings. The $^{13}$C-NMR spectrum was observed on a Varian CFT-20 Spectrometer on a solution (ca. 0.5 ml., ca. 200 mg/ml) of the sample of the antibiotic in deutero-methanol (d$_6$-MeOH). The spectrum was calibrated against internal tetramethylsilane and frequencies were recorded in ppm downfield from tetramethylsilane.

| Chromatography of Antibiotic U-64,767 | | |
|---|---|---|
| System | Rf | Detection |
| 2:1 MeOH:H$_2$O/silica gel | 0.3 | MnO$_4$/IO$_4$, bioautography |
| 1:1 MeOH:H$_2$O/silica gel | 0.5 | MnO$_4$/IO$_4$, bioautography |
| A-2 | 0.6 | Bioautography |
| 2:1:1 butanol:methanol:water | 0.8 | Bioautography |
| 6:1:1 butanol:methanol:water | 0.2 | Bioautography |

The bioautography is done using standard conditions and the bacterium *S. lutea*.

Solubilities:

Antibiotic U-64,767 is highly soluble in 1:1 methanol:-water, in glacial acetic acid and in dimethylsulfoxide. It is poorly soluble in methanol or water alone.

Antimicrobial Spectrum of Antibiotic U-64,767:

Antibiotic U-64,767 is active against various Gram-positive bacteria and *S. pneumoniae* as shown in the following tables.

Assay:

The antibacterial assay is a standard agar dilution assay. The MIC is determined by standard methods using two-fold dilutions of the antibiotic in Brain Heart Infusion Broth (Difco Lab., Detroit, Mich. One hundred μl of these dilutions are applied to ¼ inch filter paper discs and spotted on agar plates seeded with the test organisms. The plates are incubated overnight at 37° C. and then read. The lowest concentration still yielding a distinct zone of inhibition is considered the MIC for that test organism.

| Microorganism | Minimum Inhibitory Concentration (mcg/ml) |
|---|---|
| *Staphylococcus aureus* UC 76 | 25 |
| *Streptococcus pyogenes* UC 152 | 12.5 |
| *Streptococcus faecalis* UC 694 | 50 |
| *Escherichia coli* UC 45 | >400 |
| *Klebsiella pneumoniae* UC 58 | 400 |
| *Salmonella schottmuelleri* UC 126 | 400 |
| *Pseudomonas aeruginosa* UC 95 | >400 |
| *Streptococcus pneumoniae* UC 41 | 25 |

"UC" is a registered trademark of The Upjohn Company Culture Collection. These cultures can be obtained from The Upjohn Company in Kalamazoo, Mich., upon request.

THE MICROORGANISM

The microorganism used for the production of antibiotic U-64,767 is a biologically pure culture of *Streptomyces macronensis*, Dietz sp.n., NRRL 12566.

A subculture of this microorganism can be obtained from the permanent collection of the Northern Regional Research Laboratory, U.S. Department of Agriculture, Peoria, Ill., U.S.A. A viable subculture was deposited on Nov. 2, 1981. Its accession number in this depository is NRRL 12566. It should be understood that the availability of the culture does not constitute a license to practice the invention in derogation of patent rights granted with the subject instrument by governmental action.

The microorganism of this invention was studied and characterized by Alma Dietz of The Upjohn Research Laboratories.

*Streptomyces macronensis* Dietz sp. nov., NRRL 12566.

Color Characteristics: Aerial mycelium predominantly peach to pink. Melanin-positive. The color pattern on Ektachrome is given in Table 1. Reference color characteristics are given in Table 2. The culture may be placed in the Red (R) color series of Tresner and Backus [Tresner, H. D., and E. J. Backus. 1963. System of color wheels for streptomycete taxonomy. Appl. Microbiol. 11:335–338].

Microscopic Characteristics: Spore chains are long, straight, and loosely coiled at the tip. Spores are oblong, 1.5×0.6 μm or 1.5×0.2 μm when observed in a side view, and have a depressed smooth surface which gives a ridged appearance. Fourteen day cover glass preparations were used for the microscopic examinations.

Growth on Carbon Compounds: See Table 3.

Whole Cell Analysis: L-diaminopimelic acid was detected.

Culture Characteristics-General: See Table 4.

Temperature: The culture grew at 18°–45° C. on Bennett's, Czapek's sucrose, and Maltose-Tryptone agars. Optimum growth was at 24°–37° C. There was no growth at 55° C.

Antibiotic U-64,767 is produced.

Source: Soil sample from Belize.

Type Strain: *Streptomyces macronensis* sp. nov., NRRL 12566.

*S. macronensis*, NRRL 12566 appeared most similar on Ektachrome (Table 1) to *Streptomyces venezuelae* ATCC®10712 [Shirling, E. B. and D. Gottlieb. 1968. Cooperative description of type cultures of Streptomyces III. Additional species descriptions from first and second studies. Int. J. Syst. Bacteriol. 18:279–392]=NRRL 2277, the type strain [Skerman, V. B. D., V. McGowan, and P. H. A. Sneath. 1980. Approved Lists of Bacterial Names. Int. J. Syst. Bacteriol. 30:225–420]. Both cultures have long straight chains of smooth surfaced spores. The chains of spores of the new culture were frequently coiled at the tip. Both cultures are melanin-positive. The new culture is in the Red (R) series of Tresner and Backus [Tresner, H. D. and E. J. Backus, supra]; *S. venezuelae* is in the Gray (64) series. The series placement of *S. venezuelae* is variable. The culture is placed in the Gray series by ISP criteria [Shirling, E. B., and D. Gottlieb. 1966. Methods for characterization of Streptomyces species. Int. J. Syst. Bacteriol. 16:313–340] and in the *Red series (Table 17.44a)* according to Pridham and Tresner in Bergey's Manual 8th Ed. [Pridham. T. G., and H. D. Tresner. 1974. Part 17. Actinomycetes and related organisms. Family VII. Streptomycetaceae Waksman and Henrici 1943. Genus I. Streptomyces Waksman and Henrici 1943. Table 17.44a of the Red series. Pages 804–807 in Buchanan and Gibbons, eds., Bergey's Manual of Determinative Bacteriology, 8th ed. The Williams and Wilkins Co., Baltimore]. Differentiation of the cultures is made on the basis of reference color characteristics (Table 2), growth on carbon compounds in the synthetic medium of Shirling and Gottlieb [Shirling, E. B., and D. Gottlieb, supra], Table 3, and general cultural characteristics (Table 4). *S. macronensis*, NRRL 12566 has fair growth at 45° C.; *S. venezuelae* does not grow at 45° C. *S. macronensis*, NRRL 12566 has the same carbon utilization patern as *Streptomyces melanogenes* ISP-5192 [Shirling, E. B. and D. Gottlieb. 1969. Cooperative description of type cultures of Streptomyces IV. Species descriptions from the second, third and fourth studies. Int. J. Syst. Bacteriol. 19:391–512], ATCC 23826 [Pridham. T. G., and H. D. Tresner, supra]. This culture is also placed in the Red series but might be placed in the Gray series [Shirling, E. B. and D. Gottlieb. 1969, supra and Pridham, T. G. and H. D. Tresner, supra]. The culture is melanin-positive and has long straight chains of smooth-surfaced spores. The distinctive coiled-tip chains of the new culture are not reported for *S. melanogenes*. *S. macronensis*, NRRL 12566 does not have the reported bluish green vegetative mycelium on some media as is reported for *S. melanogenes*. *S. macronensis*, NRRL 12566 is differentiated from the two cultures to which it is most similar, *S. venezuelae* and *S. melanogenes*. Therefore, it is concluded that *S. macronensis*, NRRL 12566 is a distinctly different species of the genus Streptomyces for which the name *Streptomyces macronenses* Dietz sp.nov. is proposed. It is understood that in accordance with the Rules of Nomenclature of Bacteria [Lapage, S. P., P. H. A. Sneath, E. F. Lessel, V. B. D. Skerman, H. P. R. Seeliger, and W. A. Clark, ed. 1975. International code of nomenclature of bacteria, 1976 Revision. American Society for Microbiology, Washington, D.C.], this is the type strain and that should another strain be found the type strain would also be the type subspecies.

The species name selected refers to the large size of the molecule of the antibiotic produced by the culture.

TABLE 1

| | | Color Characteristics* on Ektachrome[1,2] | | | |
|---|---|---|---|---|---|
| | Deter- mina- | *S. macronensis* NRRL 12566 | | *S. venezuelae* ATCC 10712 (NRRL 2277) | |
| Agar Medium | tion | Chip | Color | Chip | Color |
| Bennett's | S | 72 | dark orange yellow | 70 | light orange yellow |
| | R | 72 | dark orange yellow | 71 | light orange yellow |
| Czapek'S sucrose | S | 7 | pale pink | 7 | pale pink |
| | R | 73 | pale orange yellow | 73 | pale orange yellow |
| Maltose- tryptone | S | 8 | grayish pink | 8 | grayish pink |
| | R | 78 | dark yellowish brown | 78 | dark yellowish brown |
| Peptone- iron | S | 59 | dark brown | 59 | dark brown |
| | R | 59 | dark brown | 59 | dark brown |
| 0.1% Tyrosine | S | 7 | pale pink | 7 | pale pink |
| | R | 70 | light orange yellow | 70 | light orange yellow |

TABLE 1-continued

| | | Color Characteristics* on Ektachrome[1,2] | | | |
|---|---|---|---|---|---|
| | Deter-mina-tion | S. macromensis NRRL 12566 | | S. venezuelae ATCC 10712 (NRRL 2277) | |
| Agar Medium | | Chip | Color | Chip | Color |
| Casein starch | S | 7 | pale pink | 7 | pale pink |
| | R | 77 | moderate yellowish brown | 77 | moderate yellowish brown |

S = Surface
R = Reverse
[1] Dietz, A. 1954. Ektachrome transparencies as aids in actinomycete classification. Ann. N. Y. Acad. Sci. 60:152-154.
[2] Dietz, A. and D. W. Thayer (ed.). 1980. Actinomycete Taxonomy (Procedures for Studying Aerobic Actinomycetes with Emphasis on the Streptomycetes). SIM Special Publication Number 6. Soc. for Ind. Microbiol., Arlington, VA.
*Growth on media in tubes was photographed after seven days incubation at 28° C. Color was determined by comparison with NBS color chips [SP 440. Color: Universal Language and Dictionary of Names. U.S. Government Printing Office, Washington, D.C. 20402.];

TABLE 2

| | | Reference Color Characteristics* | | | |
|---|---|---|---|---|---|
| | Deter-mina-tion | S. macronensis NRRL 12566 | | S. venezuelae ATCC 10712 (NRRL 2277) | |
| Agar Medium | | Chip | Color | Chip | Color |
| Bennett's | S | 39 | grayish red | 93 | gray |
| | R | 53 | moderate orange | 77 | moderate yellowish brown |
| | P | 71 | moderate orange yellow | 76 | light yellowish brown |
| Czapek's sucrose | S | 31 | pale yellowish pink | 29 | yellowish white |
| | R | 50 | strong orange | 29 | yellowish white |
| | P | — | — | — | — |
| Maltaose-tryptone | S | 10 | pinkish gray | 93 | yellowish gray |
| | R | 43 | moderate reddish brown | 78 | dark yellowish brown |
| | P | 75 | deep yellowish brown | 77 | moderate yellowish brown |
| Yeast extract-malt extract (ISP-2) | S | 31 | pale yellowish pink | 90 | grayish yellow |
| | R | 38 | dark reddish orange | 77 | moderate yellowish brown |
| | P | 71 | moderate orange yellow | 77 | moderate yellowish brown |
| Oatmeal (ISP-3) | S | 30 | dark yellowish pink | 93 | yellowish gray |
| | R | 36 | deep reddish orange | 77 | moderate yellowish brown |
| | P | — | — | 76 | light yellowish brown |
| Inorganic salts starch (ISP-4) | S | 31 | pale yellowish pink | 93 | yellowish gray |
| | R | 38 | dark reddish orange | 77 | moderate reddish brown |
| | P | — | — | 76 | light yellowish brown |
| Glycerol asparagine (ISP-5) | S | 52 | light orange | 93 | yellowish gray |
| | R | 53 | moderate orange | 77 | moderate yellowish brown |
| | P | 70 | light orange yellow | 76 | light yellow |

S = Surface
R = Reverse
P = Pigment
*Color determination was made on growth on plates incubated 14 days at 28° C. Color was determined by comparison with NBS color chips [SP 440, supra] [SRM 2106, supra].

TABLE 3

| Synthetic Medium (ISP-9) | S. macronensis NRRL 12566 | S. venezuelae ATCC 10712 (NRRL 2277) |
|---|---|---|
| Negative Control (No carbon cpd.) | +(light growth) | — |
| Positive Control (D-glucose) | ++ | + |
| L-arabinose | + | ++ |
| Sucrose | — | — |
| D-xylose | + | ++ |
| Inositol | + | — |
| D-mannitol | ++ | — |
| D-fructose | + | ++ |
| Rhamnose | — | ++ |
| Raffinose | ± | — |

TABLE 3-continued

| Synthetic Medium (ISP-9) | S. macronensis NRRL 12566 | S. venezuelae ATCC 10712 (NRRL 2277) |
|---|---|---|
| Cellulose | — | — |

+ + = Strong utilization
+ = Positive utilization
± = Doubtful utilization
− = No utilization

TABLE 4

Culture Characteristics - General

| Medium | Determination | S. macronensis NRRL 12566 | S. venezuelae. ATCC 10712 (NRRL 2277) |
|---|---|---|---|
| Agar | | | |
| Peptone-iron | S | trace pale peach | gray with colorless edge |
|  | R | brown | brown |
|  | P | brown | brown |
|  | O | melanin positive | melanin positive |
| Calcium malate | S | pale peach | very pale gray |
|  | R | orange | pale yellow cream |
|  | P | — | — |
|  | O | malate solubilized | malate slightly solubilized |
| Glucose asparaginase | S | pale peach | colorless vegetative growth |
|  | R | orange | pale yellow cream |
|  | P | very pale orange | pale pink |
| Skim milk | S | pale peach | wrinkled yellowish vegetative growth |
|  | R | center orange; edge brown | orange-tan |
|  | P | light tan | orange-tan |
|  | O | casein not solubilized | casein solubilized |
| Tyrosine | S | very pale peach | pale gray-pink |
|  | R | brown | light brown |
|  | P | tan brown | light brown tan |
|  | O | tyrosine solubilized | tyrosine solubilized |
| Xanthine | S | pale peach | pale gray-pink |
|  | R | orange | light tan |
|  | P | — | very pale tan |
|  | O | xanthine solubilized | xanthine solubilized |
| Nutrient starch | S | pale peach | pale gray pink |
|  | R | orange | cream-tan |
|  | P | — | very pale tan |
|  | O | starch not solubilized | starch not solubilized |
| Yeast extract-malt extract | S | pale peach | pale gray-pink |
|  | R | orange | light tan |
|  | P | yellow | light tan |
| Peptone-yeast extract-iron (ISP-6) | S | colorless vegetative | colorless vegetative |
|  | R | brown | brown |
|  | P | brown | brown |
|  | O | melanin positive | melanin positive |
| Tyrosine (ISP-7) | S | peach-orange | pale gray |
|  | R | red | light tan brown |
|  | P | trace yellow brown | trace yellow brown |
|  | O | melanin negative | melanin negative |
| Broth | | | |
| Synthetic nitrate | S | — | trace gray aerial on surface pellicle |
|  | P | — | — |
|  | O | compact bottom growth | compact bottom growth |
|  |  | nitrates reduced | nitrates not reduced |
| Nutrient | S | — | gray aerial on surface pellicle |
|  | P | — | tan |
|  | O | compact bottom growth | compact bottom growth |
|  |  | nitrates not reduced | nitrates reduced |
| Litmus milk | S | brown surface ring | gray aerial on brown surface ring |
|  | P | — | maroon |
|  | O | no change pH 6.82 | peptonization litmus reduced pH 7.5 |
| Gelatin | | | |
| Plain | S | orange vegtative | colorless vegetative |
|  | P | brown ¼-½ | brown ¼ |
|  | O | no liquefaction | complete liquefaction |
| Nutrient | S | pale gray aerial on surface ring | — |
|  | P | brown at surface diffused throughout medium | — |
|  | O | no liquefaction | no liquefaction |

S = Surface (aerial growth unless otherwise noted)
R = Reverse
P = Pigment
O = Other characteristics The compound of the invention process is produced when the elaborating organism is grown in an aqueous nutrient medium under submerged aerobic conditions. It is to be understood, also, that for the preparation of limited amounts surface cultures and bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distillers' solids, animal peptone liquors, meat and bone scraps, and the like. Combinations of these carbon and nitrogen sources can be used advantageously. Trace metals, for example, zinc, magnesium, maganese, cobalt, iron, and the like, need not be added to the fermentation media since tap water and unpurified ingredients are used as components of the medium prior to sterilization of the medium.

Production of the compound by the invention process can be effected at any temperature conducive to satisfactory growth of the microorganism, for example, between about 18° and 40° C., and preferably between about 20° and 28° C. Ordinarily, optimum production of the compound is obtained in about 3 to 15 days. The medium normally remains alkaline during the fermentation. The final pH is dependent, in part, on the buffers present, if any, and in part on the initial pH of the culture medium.

When growth is carried out in large vessels and tanks, it is preferable to use the vegetative form, rather than the spore form, of the microorganism for inoculation to avoid a pronounced lag in the production of the compound and the attendant inefficient utilization of the equipment. Accordingly, it is desirable to produce a vegetative inoculum in a nutrient broth culture by inoculating this broth culture with an aliquot from a soil, liquid $N_2$ agar plug, or a slant culture. When a young, active vegetative inoculum has thus been secured, it is transferred aseptically to large vessels or tanks. The medium in which the vegetative inoculum is produced can be the same as, or different from, that utilized for the production of the compound, so long as a good growth of the microorganism is obtained.

A variety of procedures can be employed in the isolation and purification of the compound produced by the subject invention from fermentation beers. Isolation can be accomplished by adsorption on non-ionic macroporous resins. Ultrafiltration, cellulose chromatography (gradient elution) and gel permeation chromatography on G-25 Sephadex can be used to purify crude preparations of the antibiotic.

In a preferred recovery process, the compound produced by the subject process is recovered from the culture medium by separation of the mycelia and undissolved solids by conventional means, such as by filtration or centrifugation, and resin adsorption of the filtered broth. The antibiotic of the subject invention can be recovered from the filtered beer by resin sorption on a resin comprising a non-ionic macroporous copolymer of styrene cross linked with divinylbenzene. Suitable resins are Amberlite XAD-2, XAD-4 and XAD-7, according to the procedure disclosed in U.S. Pat. No. 3,515,717. (Amberlite resins are available from Rohm and Haas, Philadelphai, PA.). The antibiotic can be eluted from said resins by using acetone.

Resins other than XAD-2, XAD-4 and XAD-7 may be substituted. Charcoal can also be used. Extraction with a solvent like 1-butanol also can be used.

The eluting solvent from the resins will vary from resin to resin. In general, combinations of water and a water-miscible solvent such as methanol, ethanol, tetrahydrofuran, diethylformamide or diethylsulfoxide are useful. The amount of organic solvent will vary from 5 to 95% (v/v).

Purification of the antibiotic from the resin eluate can be done by the procedures listed above, i.e. ultrafiltration, cellulose chromatography, and gel permeation chromatography.

The following examples are illustrative of the process and product of the invention, but are not to be construed as limiting. All percentages are by weight and all solvent mixture proportions are by volume unless otherwise noted.

EXAMPLE 1

A. Fermentation

A biologically pure culture of *Streptomyces macronensis* Dietz sp.n. NRRL 12566, is used to inoculate 500-ml. Erlenmeyer pre-seed flasks containing 100 ml of sterile medium consisting of the following ingredients:

|  | g/liter |
| --- | --- |
| Cerelose | 1.0 |
| Dextrin | 3.0 |
| Glycerol | 20.0 |
| Brewers yeast | 1.0 |
| Cornsteep liquor | 3.0 |

-continued

|  |  |
| --- | --- |
| Solulac[1] | 4.0 (G. P. Co.) |
| Pharmamedis[2] | 4.0 (Traders) |
| $NH_4NO_3$ | 2.0 |
| NaCl | 5.0 |
| $CaCO_3$(P-6) | 4.0 |
| (add after pH adjustment) | |
| Mineral salt solution A* | 1 ml/l |
| Mineral salt solution B** | 1 ml/l |
| *Mineral Salt Solution A | g/100 ml |
| $MgSO_4.7H_2O$ | 5.0 |
| $MnSO_4.H_2O$ | 0.30 |
| $FeSO_4.7H_2O$ | 1.0 |
| $ZnSO_4.7H_2O$ | 0.30 |
| $CoCl_2.6H_2O$ | 0.10 |
| Distilled Water (about 90 ml) | |
| Adjust pH to 2.0 with dilute sulfuric acid | |
| Add distilled water to make 100 ml | |
| **Mineral Salt Solution B | g/100 ml |
| $KH_2PO_4$ | 5.0 |
| KCl | 10.0 |
| use distilled water and make to volume. | |

[1]Solulac is a yeast based protein source (derived from grain processor and distiller residues). Supplied by Grain Processing Co., Muscatine, Iowa.
[2]Pharmamedia is an industrial grade of cottonseed flour produced by Traders Oil Mill Company, Fort Worth, Texas The preseed inoculum is grown for three days at 28° C. on a Gump rotary shaker operating at 250 rpm and having a 2½ inch stroke.

Preseed inoculum (300 ml), prepared as described above, is used to inoculate a 30 l seed tank containing 20 l of sterile medium as used above.

The inoculated seed medium is incubated at a temperature of 28° C. for 2 days with agitation at 350 rpm and air sparged in at 8 l/min with a back pressure of 8 psig.

Seed inoculum (5% seed), prepared as described above, is used to inoculate a 400 l fermentation tank containing 250 l. of sterile medium as used above. The inoculated fermentation medium is incubated at a temperature of 32° C. for 1-2 days with agitation at 250 rpm and air sparged in at 200 l/min with the back pressure at 9 psig.

A typical 22.5 hour fermentation has the following titers of antibiotic in the fermentation broth:

| Hours | Assay, *S. lutea* (zone size in mm) |
| --- | --- |
| 0 | — |
| 22.5 | 25 |

The assay is a *Sarcina lutea* agar plate diffusion assay using 0.1 M Tris.HCl buffer, pH 7.0 as diluent.

B. Recovery

To whole beer (ca. 9 l) from a fermentation, as described above, is added 2 liters of diatomaceous earth (dicalite) at harvest pH 6.5. This slurry is filtered over a bed of Dicalite 4200 with suction. The cake is washed with 1 liter of deionized water to give 10 liters of clear beer.

Assay: Filtered beer=26 mm (vs. *S. lutea*—zone size).

XAD-2 Sorption

The above filtered beer is passed over a column of XAD-2 resin which measures 5.5×60 cm at the highest flow rate possible (about 6 bed volumes/hr). The column is washed with 4 liters of deionized water and eluted with 4 liters each of 1:3 and 1:1 acetone:water in succession.

| Sample | Assy: Volume | S. lutea sensitive |
| --- | --- | --- |
| Filtered beer | 10 liters | 26 mm (zone size) |
| Spent | 10 | NZ (no zone) |
| Wash | 4 | NZ |
| 1st eluate | 4 | NZ |
| 2nd eluate | 4 | 30 mm |

The acetone is removed from the second eluate to give 1.9 liters aqueous which assays at 12 BU/ml or 75% of the original beer activity.

A BU (biounit) is defined as the concentration of the antibiotic which gives a 20 mm zone of inhibition in the agar diffusion assay when 100μ are loaded onto a 12.7 mm pad.

C. Purification

An aqueous concentrate, obtained as described above, is padded over a PM 30 ultrafilter until only 200 ml remain in the retentate (from 2.7 liters). The retentate is diluted to 2.2 liters and the filtration is repeated. The second retentate contains little activity and much dark color and is discarded.

The first PM 30 filtrate is concentrated to 300 ml on a UM 10 ultrafilter. The filtrate (2.2 liters) gives a 19 mm zone against *S. lutea* sensitive and is discarded. The retentate (diluted to 800 ml) gives a 31 mm zone against *S. lutea* sensitive. This is lyophilized to give 878 mg tan solid assaying 8 BU/mg against *S. lutea* sensitive.

The second PM 30 filtrate is concentrated over the UM 10 filter in the say way. The solids amounted to 734 mg at 8 BU/mg.

This "sieved" material is lyophilized to give a solid preparation which is treated further.

PM 30 and UM 10 filters are two of a series of filter membranes made by the Amicon Corp. (Lexington, MA. 02173). They belong to the Diaflo ® series and are used with stirred cells, also made by Amicon.

DEAE Cellulose Column (Supplied by Whatman Chemical Separations, Inc.)

A 2.5×100 cm column is slurry-packed with Whatman DE-52 (DEAE) cellulose in 1:1 MeOH:H$_2$O (v/v). A solution of "sieved" product in the same solvent (15 ml) is injected and the column is eluted isocratically. The dark color sticks to the top of the column while the antibiotic U-64,767 comes through just after the void volume. The methanol is removed on a rotary evaporator and the aqueous solution is lyophilized. This gives essentially pure antibiotic U-64,767 as an amorphous solid having a white color.

We claim:

1. A process for preparing antibiotic U-64,767 which in its essentially pure crystalline form has the following characteristics:
    (a) molecular weight of 1191 (mass spectrometry);
    (b) color and form of pure solid: white
    (c) is highly soluble in 1:1 water:methanol and in glacial acetic acid and poorly soluble in methanol or water alone;
    (d) a characteristic $^{13}$C-NMR spectrum as shown in FIG. 3 of the drawings;
    (e) a characteristic UV spectrum with a maximum absorption at 223 nm
    (f) a characteristic infrared absorption spectrum when dissolved in a mineral oil mull as shown in FIG. 1 of the drawings;
    (g) has a molecular formula $C_{57}H_{109}N_1O_{24}$; and
    (h) a melting point of 153°–155° C. with decomposition, which comprises cultivating *Streptomyces macronensis* Dietz sp.n., NRRL 12566, in an aqueous nutrient medium under aerobic conditions until substantial antibiotic U-64,767 activity is imparted to said medium.

2. A process, according to claim 1, wherein said aqueous nutrient medium contains a source of assimilable carbohydrate and assimilable nitrogen.

3. A process for recovering antibiotic U-64,767 from a fermentation beer according to claim 2 which comprises:
    (a) filtering said beer to obtain filtered beer containing antibiotic U-64,767;
    (b) adsorbing antibiotic U-64,767 from said filtered beer by passing said beer through a non-ionic macroporous resin;
    (e) eluting antibiotic U-64,767 from said resin with a solvent for antibiotic U-64,767 to obtain an eluate containing antibiotic U-64,767; and
    (d) purifying said elutate by chromatographic means to obtain essentially pure antibiotic U-64,767.

4. A biologically pure culture of the microorganism *Streptomyces macronensus* Dietz sp.n., NRRL 12566.

* * * * *